United States Patent [19]
Kostich

[11] Patent Number: 5,081,665
[45] Date of Patent: Jan. 14, 1992

[54] DEVICE FOR HOLDING A HEAD IN A PRONE OR SUPINE POSITION

[75] Inventor: Jeffrey V. Kostich, Akron, Ohio

[73] Assignee: Julia Kostich, Akron, Ohio

[21] Appl. No.: 496,895

[22] Filed: Mar. 16, 1990

[51] Int. Cl.$^5$ ............................................. H05G 1/02
[52] U.S. Cl. ..................................... 378/208; 378/20; 378/68; 128/76 R; 128/845; 128/869
[58] Field of Search .................. 128/76 R, 845, 869; 378/208, 205, 204, 20, 68

[56] References Cited

U.S. PATENT DOCUMENTS

| | | | |
|---|---|---|---|
| 3,897,777 | 8/1975 | Morrison | 378/208 |
| 4,256,112 | 3/1987 | Kopf et al. | 378/208 |
| 4,463,758 | 8/1984 | Patil et al. | 378/208 |
| 4,841,965 | 6/1989 | Jacobs | 378/208 |

Primary Examiner—Edward P. Westin
Assistant Examiner—David P. Porta
Attorney, Agent, or Firm—Oldham & Oldham Co.

[57] ABSTRACT

A device for holding, positioning and immobilizing a human head in prone or supine positions during medical treatments or examinations. One or more arcuate shaped support plates receive the head and related support assemblies, attached to the support plates, maintain the head in a fixed position. The device is composed of radiolucent material in order that such device can be used during X-rays, CAT scans, radiation therapy and other treatment or examination procedures.

28 Claims, 4 Drawing Sheets

DEVICE FOR HOLDING A HEAD IN A PRONE OR SUPINE POSITION

TECHNICAL FIELD

The present invention relates to a device for holding and positioning the skull of a human or other primate when placed in a prone or supine position. More specifically, this invention relates to a radiolucent device, used to hold or position a skull in a prone or supine position during X-Ray, CAT, radiation therapy or other examination procedures. This device achieves such positioning by supporting the frontal bone and the mandible with support structures.

DISCUSSION OF THE PRIOR ART

Advances in technology have enabled physicians and technicians to identify injury, diagnose disease, monitor bodily function through the use of X-Ray, CAT-Scan, MRI and other radiographic procedures and therapeutically treat patients using external radiation. Often because of the patient's injury or the nature of the procedure, such examinations must be done with the patient in a supine or prone position. While in this position, the patient must normally remain still for the duration of the procedure. Especially if the examination is of the skull or cervical region holding, such a position for the time necessary may be difficult and uncomfortable, if not impossible.

Several devices have been developed to assist medical personnel in maintaining the head and neck of a patient in proper position required for treatment or examination. Many of these devices limit their use to positioning the head with the body in a supine position. Many of these devices are foam, rubber or plastic blocks of various shapes which have depressions formed therein.

There are very few devices which can be used when the patient is required to maintain a prone or supine position. A number of the devices used in supine positioning were tried in prone positioning but with limited success.

Several of the blocks mentioned above were formed with a hole in the center of the depressed area to allow a space for the patients mouth and nose when in a prone position. These devices are not popular with patients because it is somewhat difficult to breath during the examination and the device creates anxiety in patient's who fear a possibility of suffocation. For this type of examination, a number of medical personnel use an axial head-holder assembly not intended or designed for prone use and position the head by inserting foam wedges between the assembly and the patient's head. This method can be uncomfortable, does not provide predictable and consistent support, and requires the operator to maintain an inventory of foam wedges.

SUMMARY OF THE INVENTION

In light of the foregoing discussion, therefore, a novel device for holding and positioning a human head in a prone position is herein presented. The device was developed primarily for use during various medical treatments with radiation and other procedures. The device generally supports the frontal and mandibular portions of the skull. The various supports may be adjusted for supporting the head in a number of prone or supine positions and can also be adjusted to accommodate patients with a range of head sizes.

It is, therefore, an object of the present invention to provide a device for holding and positioning a human head in the prone or supine position.

It is a further object of the present invention to provide a device for holding and positioning a human head in the prone or supine position, said device which is radiolucent.

It is a further object of the present invention to provide a device for holding and positioning a human head in the prone or supine position which provides support superior to that found in the prior art.

It is a further object of the present invention to provide a device for holding and positioning a human head in the prone or supine position which can monitor the breathing of a prone positioned patient.

It is still a further object of the present invention to provide a device for holding and positioning a human head in the prone or supine position which is more comfortable and less threatening than the prior art.

It is still a further object of the present invention to provide a device for holding and positioning a human head in the prone position which provides a means of adjustment for supporting the head and cervical region in numerous positions.

It is still a further object of the present invention to provide a device for holding and positioning a human head in the prone position which is adjustable to accommodate various skull and neck sizes.

These and other objects and advantages of the present invention will become more readily apparent from the more detailed description of the preferred embodiments taken in conjunction with the drawings wherein similar elements are identified by like numerals through several views. Such objects and advantages are achieved by a device for holding a head in a prone position comprising a base, having a top and bottom surface, at least two support units, positioned on the top surface of said base, each unit comprising an arcuate shaped plate for receiving at least a portion of said head, a brace for supporting said plate, a means for retaining each said support unit in a fixed position and a means for connecting said cross-brace to said retaining means.

BRIEF DESCRIPTION OF THE DRAWINGS

In order to better understand the present invention, reference is made to the accompanying drawings, wherein.

DETAILED DESCRIPTION OF THE PREFERRED EMBODIMENT

Figure 1:
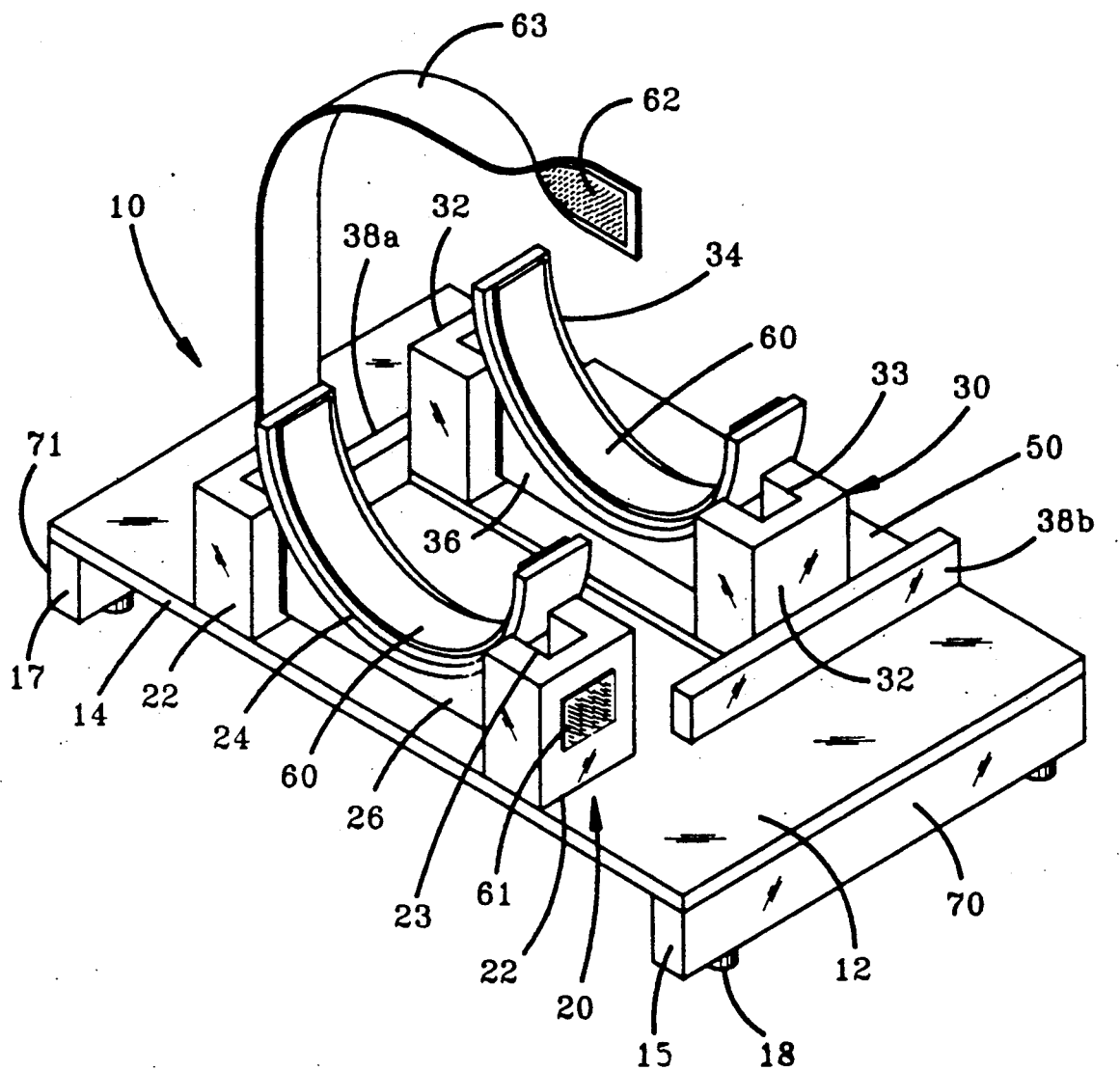
FIG. 1 is a perspective view of a device for holding a human head in a prone position.

This invention will be described in detail with reference to the preferred embodiment thereof. Like elements are identified by like reference numerals throughout the drawings and specification.

Now, with reference to FIG. 1, the device 10 for holding a head in a prone or supine position according to the present invention comprises generally a base 12, a frontal support 24, a frontal support frame 22, a mandibular support 34, a mandibular support frame 32, and a means for horizontal adjustment 36. The present invention is designed to be used to support and position the human head in a prone or supine position during any number of radiographic and other medical procedures and examinations.

A primary use of the present invention is the positioning and immobilizing of a patient's head in the required "set up" position for radiation therapy treatments of the head and neck region. Additionally the device 10 is used to position the head for treatments or examinations including the thorax region or various positions of the central nervous system.

The various components of a device 10 are preferably made of a radiolucent material such as acrylic, nylon and copolymers thereof to permit use with radiographic procedures. However, device 10 can be constructed of other materials such as plastics, fiberglass or various metals if radiolucency is not required. The preferred material for this embodiment is transparent acrylic.

The base 12 is illustrated as being rectangular in shape, although a base of virtually any shape is contemplated. The base 12 is rigid, possesses substantial strength to support the other components and the weight of a human head during examination, and has a preferable thickness ranging from about $\frac{1}{8}"-\frac{1}{2}"$. The underside of base 12 discloses a plurality of rubber grommets 18 to prevent the device 10 from sliding when placed on a planar surface. Any number, shape or size grommets may be made using any suitable material known in the art. To further stabilize the unit 10 during use, certain embodiments can include one or more flanges attached to and extending downward from base 12. FIG. 1 illustrates flanges 70 and 71 as attached to edges 15 and 17 of base 12. Such flanges 70 and 71 are designed to pass along each side of a standard treatment table to prevent movement during examination or treatment. Flanges 70 and 71 can be permanently attached or removable. Flanges 70 and 71 also have rubber grommets along their bottom surface to prevent sliding on surfaces when the device 10 is not in use.

With further reference to FIG. 1, the preferred embodiment discloses a frontal support 20 secured to base 12 adjacent to longitudinal edge 14. Frontal support 20 comprises a frontal support frame 22, a brace 26, two support legs 25 and a frontal support plate 24. The frontal support frame comprises two blocks, 22a and 22b placed parallel to one another, adjacent to longitudinal edge 14, and at a distance from the other. Each block, 22a or 22b, has a vertical slot cut therein having an open side and having a length substantially equal to the height of said block. Each slot 23 is formed on the inner surface of said block 22 and such slots oppose one another, such that blocks 22a and 22b appear as mirror images to one another. Blocks 22a and 22b are secured to base 12 by any means known in the art consistent with maintaining radiolucency when desirable.

Cross-brace 26 is an essentially rectangular shaped block having a thickness approximately equal to the width of slot 23 and a length just slightly less the distance between blocks 22a and 22b. Brace 26 has a semi-circular cut in the top edge across the length to receive said frontal support plate 24. Support plate 24 is a rectangular plate arcuately formed by drawing the opposite ends towards a midpoint to form a semicircle. This support plate 24 is dimensioned to seat in the semi-circular arc formed in cross-brace 26. Cross brace 26 further comprises one or more slots formed near the bottom of cross-brace 26 directly opposite slot 23 to receive support legs 25.

Figure 4:
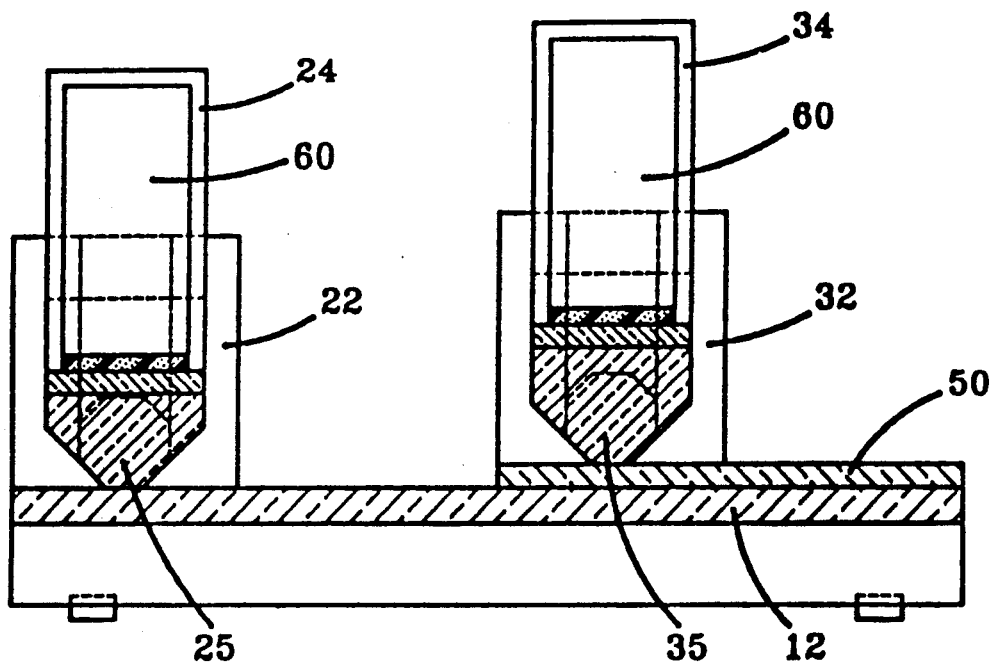
FIG. 4 is a cross sectional side view of a device for holding a human head in a prone position as taken through line 4—4 in FIG. 3.
Figure 4A:
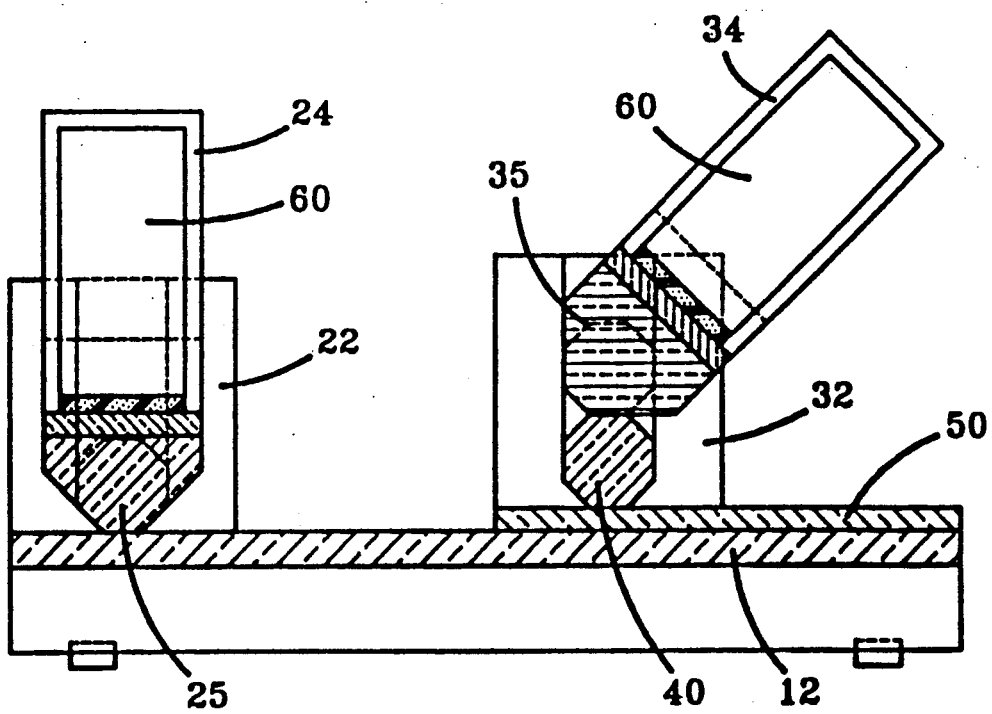
FIG. 4a is a cross-sectional side view of a device for holding a human head in a prone position as taken through line 4—4 in FIG. 3 illustrating a support structure in an adjustable position.

Support legs 25 preferably have a regular octagonal shape in transverse cross-section and are better illustrated in FIG. 4 and 4a. One end of each support leg 25 is seated in the slot formed in the base of said cross brace 26. Each support leg 25 is of sufficient length so as to enter a substantial depth of slot 23 in blocks 22a and 22b. Each support leg 25 is dimensioned such that a diameter taken through two parallel sides of the octagonal cross-section is just slightly less than the width of said slot 23. Cross legs 25 are attached to cross brace 26 so that corresponding sides of each leg are parallel to another.

Cross brace 26, having two support legs 25 and a frontal plate 24 attached as described above, is positioned between frontal support blocks 22a and 22b such that each support leg slidably engages a slot 23 in block 22a or 22b. An alternative embodiment contemplates support leg 25 as a single dowel wherein each end of the dowel engages one slot in either block 22a or 22b.

While support leg 25 is illustrated as octagonal in shape, any number of shaped dowels are contemplated such as rectangular, circular or hexagonal.

Mandibular support 30 is virtually identical in construction to frontal support 20. It comprises a mandibular support frame 32, a brace 356, two support legs 35 and a mandibular support plate 34.

Mandibular support 30 and frontal support 20 are illustrated as having similar dimensions although one or both of these supports may vary in size depending on the procedure in which this device is utilized and the size and weight of the person undergoing the procedure. Frontal support 20 and mandibular support 30 as shown in FIG. 4 are positioned such that cross braces 26 and 36 attached to frontal support plate 24 and mandibular support plate 34 are vertical and aligned perpendicular to base 12. It is desirable that such supports have the capability of adjustment to vary the position of the patient's head and neck region to be examined. Each support 20 and 30 can be angled in either direction from its standard vertical position. This is accomplished by removing the support from the slots in support frame 22 or 32 rotating the support to its desired position and introducing the support legs 25 or 35 back into the slots in the respective support frame and lowering the support into position such that the support legs come to rest with a new side in contact with the bottom of its respective slots as illustrated in FIG. 4a.

The embodiment illustrated in FIG. 4 and 4a, therefore, disclose each support as having up to five positions around an arc of 180°. More varied angles are possible with an embodiment wherein support legs, 25 or 35 are cylindrical. In this embodiment, position of the support is maintained with an set screw inserted into a hole in the blocks of support frames 22 and 32 wherein such screw is tightened against support leg to hold support in position.

An alternative embodiment is contemplated, wherein support legs 25 and 35 are not attached to cross braces 26 and 36. In this embodiment the cross-braces 26 and 36 slidably engage slots 23 and 33. This embodiment may be utilized in cases where adjustability of the support plates 24 and 34 is not desired as cross braces 26 and 36 are maintained in a position perpendicular to the base 12.

The vertical position of each support assembly may be elevated from its standard position in FIG. 4 by a spacing dowel 40 illustrated in FIG. 4a. Spacer dowel 40 is dimensioned similar to support legs 25 or 35. Spacer dowel 40 has a diameter slightly less than the width of slots 23 or 33 and a length sufficient so as to simultaneously engage both slots of support frame 22 or 32. Spacer dowel 42 is disclosed octagonal in shape but dowels of virtually any shape may be used. A plurality of rectangular dowels having a width slightly less than the width of slots 23 or 33, but varying heights may be used.

Figure 2:
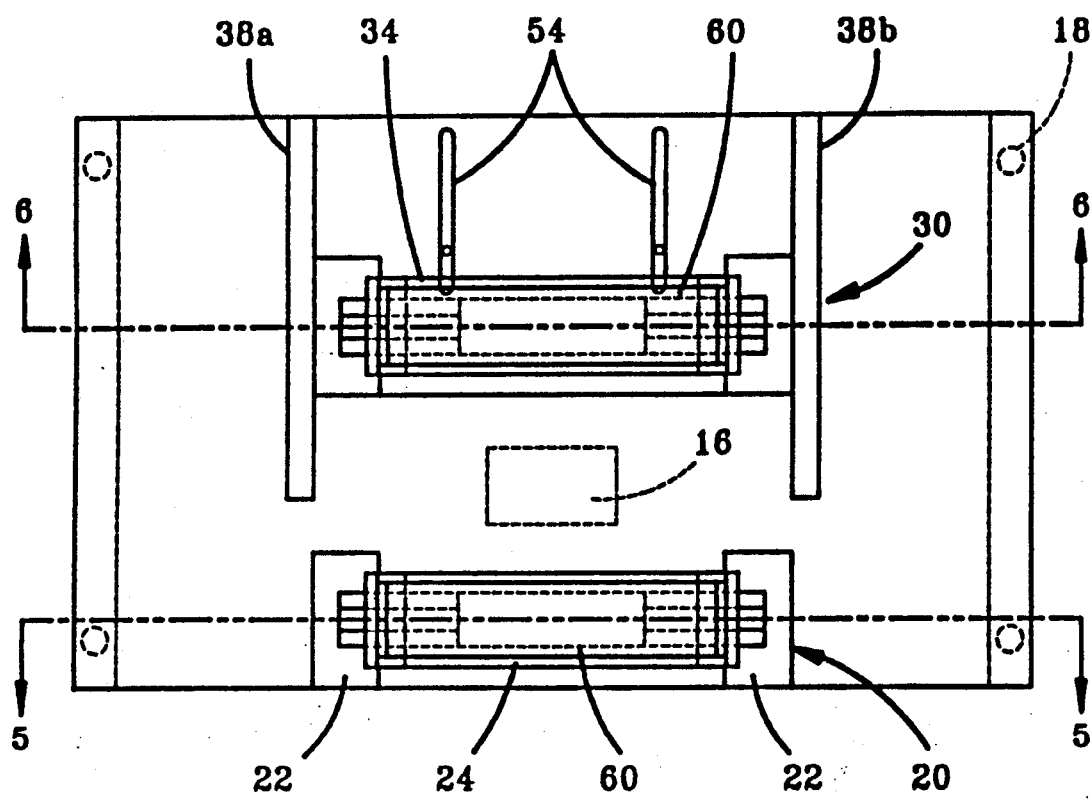
FIG. 2 is a top view of a device for holding a human head in a prone position.

It is also desirable that device 10 have the capability of varying the distance between each support assembly. Such adjustability is achieved by placing at least one support assembly on a horizontal sliding plate 50 as shown in FIG. 4. Horizontal sliding plate 50 is placed over base 12 and alignment is maintained by walls 38a and 38b. Lateral movement is prevented by track pins 52 which engage slots 54 formed in base 12, as shown in FIG. 2.

Figure 5:
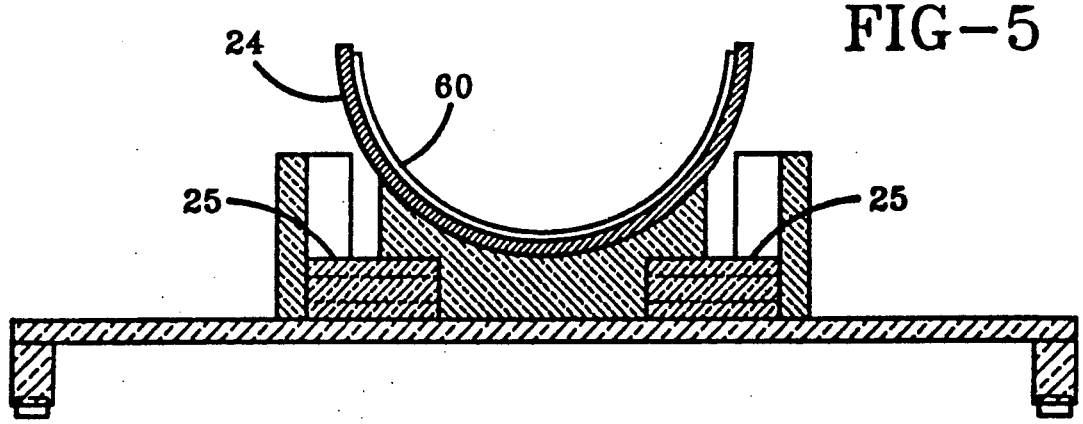
FIG. 5 is a transverse cross-sectional view of a support structure in a device for holding a human head in a prone position as taken through line 5—5 in FIG. 2.
Figure 6:
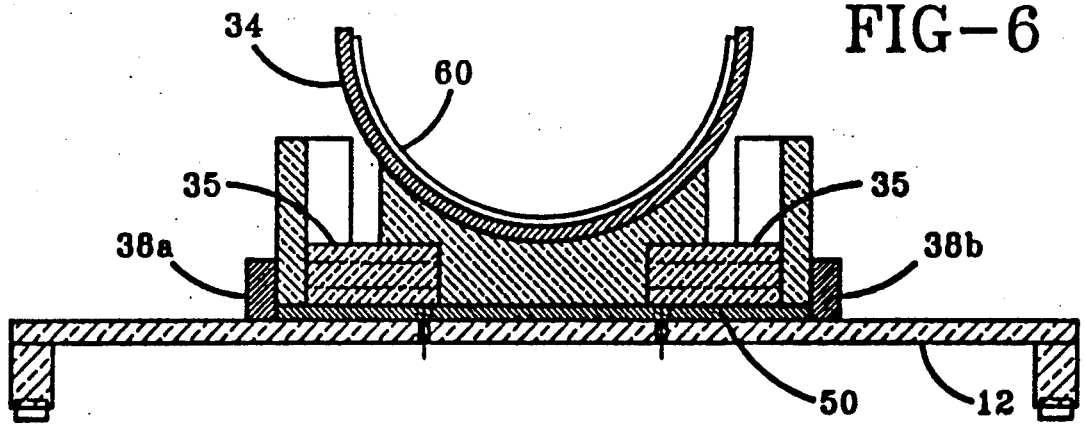
FIG. 6 is a transverse cross-sectional view of a support structure in a device for holding a head in a prone position as taken through line 6—6 in FIG. 2. a support
Figure 6A:
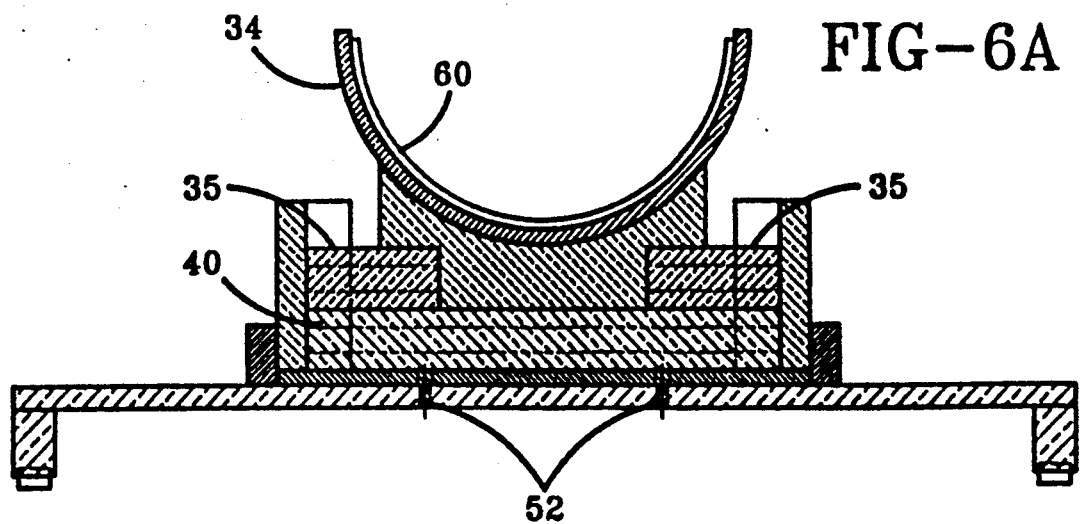
FIG. 6a is a transverse cross-sectional view of structure in a device for holding a human head in a prone position illustrating an alternate positioning of a support structure.

FIGS. 5, 6, and 6a show cross-sectional views of device 10 from various angles. FIG. 6a illustrates a cross-sectional view of mandibular support 30 with spacer dowel 40.

Figure 3:
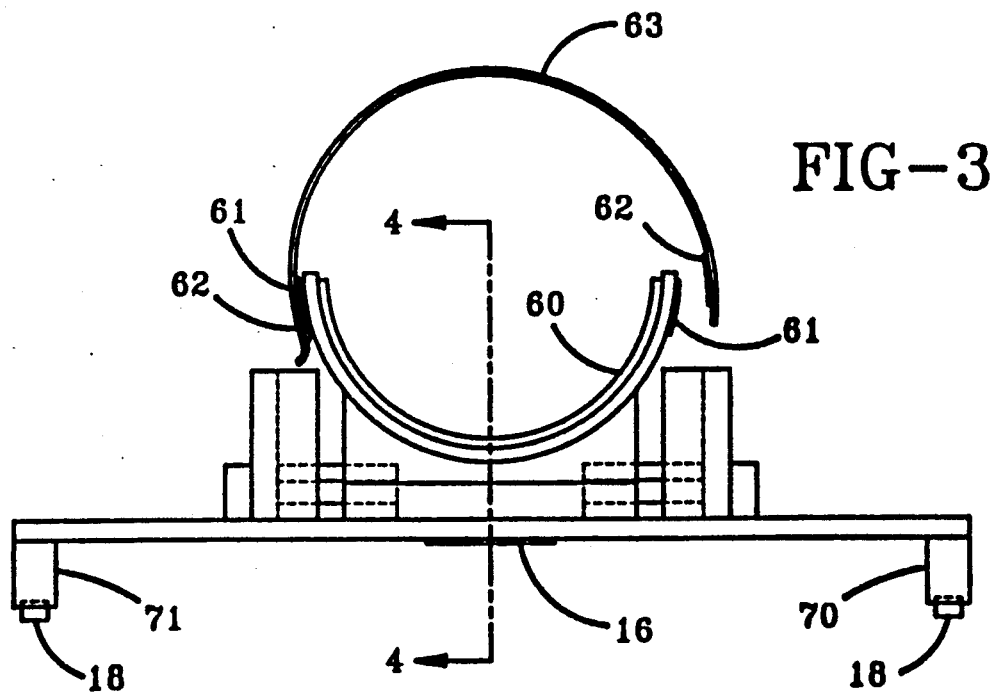
FIG. 3 is a front view of a device for holding a human head in a prone position.

The preferred embodiment discloses two support assemblies. Support assemblies 20 and 30 are aligned parallel to each other and located at similar distances from edges 15 and 17. These support assemblies, 20 and 30 serve to hold a human head in a prone position for examination and other medical procedures. Support plates 24 and 34 are designed to be positioned at a vertical distance above the base which is sufficient to allow placement of patient's nose and mouth between these assemblies. It is contemplated that a layer of cushioning material 60, shown in FIG. 3, may be disposed on the upper surface of each support plate to make the positioning of the patient's head more comfortable to the patient. It is further contemplated that such cushioning material 60 be removable as sanitary conditions would require that such material be replaced with each use. A preferred means of cushioning involves adhering one or more hook and loop fasteners to the upper surface of each support plate and attaching a corresponding piece of hook and loop fastener to the underside of the cushioning material 60.

Device 10 also includes a means for monitoring the patient's breathing when the patient is placed in the prone position. A preferred means for monitoring the patient's breathing includes placing an area of colored material 16 on the underside of the base 10, such that the colored material 16 can be seen from the opposite side of the base 10. This material is placed such that it appears in the region of the base between the frontal and mandibular supports 30 and 20. As the patient breathes, the patient's breath fogs the acrylic base and the colored material cannot be viewed. However, if the patient's breathing should stop this area of the base would not fog and the colored square would be visible from the surface of the base 10. The size, shape and color of the monitoring means 16 could vary greatly. Such a monitoring means 16 provides a simple but reliable means for technicians, physicians and nurses to monitor patient breathing during prone positioning.

While the primary use of device 10 is for use for prone positioning it is contemplated that this same device 10 can be used for supine positioning of patients. Furthermore, device 10 can be made in varying sizes for use with infants, pediatrics and adults. While not desirable unless necessary, a restraining means for maintaining the patient's head and neck in position during the examination may be utilized. Such restraining means could be attached to the support plates 24 or 34 as shown in FIG..3, or support frame 22 or 32 as shown in FIG. 1, by any conventional means known in the art. The preferred embodiment, shown in FIG. 1, discloses a strap 63 utilizing corresponding lengths of hook and loop fasteners 61 and 62 as a means to secure the patient's head in the designated position. The strap 63 can be made from any variety of materials known in the art including cloths, nylon, vinyl and others. However, it is desirable that such straps be disposable or capable of cleaning between patients to assure the maintenance of sanitary conditions. Additionally, it is contemplated that a layer of cushioning material can be disposed on the inner surface of strap 63 so as to contact the patients head and provide comfort while the strap 63 is in place.

While in accordance with the patent statutes the best mode and preferred embodiment of the invention has been described, it is to be understood that the invention is not limited thereto, but rather is to be measured by the scope and spirit of the appended claims.

What is claimed is:

1. A device for holding a patient's head in a prone or supine position comprising:
   a base having a top and bottom surface,
   at least two support members each comprising an essentially arcuate shaped plate and a brace for supporting said plate, each brace having opposite ends and opposite sides, and
   at least one support frame for retaining each support member in a fixed position, each support frame positioned on the top surface of said base and comprising two spaced end portions having an inner and outer surface and an open slot cut in the inner surface of each end dimensioned to engage at least a portion of said brace.

2. A device for holding a patient's head in a prone or supine position according to claim 1 wherein said support frames are in essentially parallel alignement and registry with one another.

3. A device for holding a patient's head in a prone or supine position according to claim 1 wherein said brace has a length less than the distance between the two spaced ends of said support frame and further comprises a connecting means extending outward from at least one end of said brace and is adapted to engage a slot in an end portion of said support frame.

4. A device for holding a patient's head in a prone or supine position according to claim 1, wherein each end of said brace has a thickness slightly less than the width of a slot in said support frame, such that each end of said brace slidably engages a slot in an end portion of said support frame.

5. A device for holding a patient's head in a prone or supine position according to claim 3 wherein said connecting means comprises at least one dowel extending outward from an end of said brace, each dowel having a diameter slightly less than the diameter of said slot and sufficient length to slidably engage a slot of in one end portion of said support frame.

6. A device for holding a patient's head in a prone or supine position according to claim 5 wherein said connecting means comprises a dowel extending outward from each end of said braces.

7. A device for holding a patient's head in a prone or supine position according to claim 5 wherein said at least one dowel has essentially on octagonal transverse cross-section.

8. A device for holding a patient's head in a prone or supine position according to claim 5 wherein said at least one dowel has an essentially hexagonal transverse cross-section.

9. A device for holding a patient's head in a prone or supine position according to claim 5 wherein said at least one dowel has a cylindrical shape.

10. A device for holding a patient's head in a prone or supine position according to claim 1 further comprising a means for varying the distance between support frames.

11. A device for holding a patient's head in a prone or supine position according the claim 10 where said means for varying the distance further comprises a plate to which at least one support frame is attached, said plate slidably moves in a direction essentially parallel to the top surface of said base.

12. A device for holding a patient's head in a prone or supine position according to claim 1 wherein at least one support frame comprises a means for vertical adjustment.

13. A device for holding a patient's head in a prone or supine position according to claim 12 wherein said vertical adjustment means comprises a means for repositioning said connecting means within said slot.

14. A device for holding a patient's head in a prone or supine position according to claim 3 wherein said means for vertical adjustment is at least one dowel of sufficient length so as to engage a slot in each block of one support frame.

15. A device for holding a patient's head in a prone or supine position according to claim 14 wherein said at least one dowel is cylindrical.

16. A device for holding a patient's head in a prone or supine position according to claim 14 wherein said at least one dowel is octagonal.

17. A device for holding a patient's head in a prone or supine position according to claim 14 wherein said at least one dowel is rectangular.

18. A device for holding a patient's head in a prone or supine position according to claim 14 wherein said at least one dowel is hexagonal.

19. A device for holding patient's head in a prone or supine position according to claim 1 wherein each support member comprises a means for adjusting the arcuate position of said member.

20. A device for holding a patient's head in a prone or supine position according to claim 1 wherein said device further comprises a means for monitoring the breathing of said patient's head when in a prone position.

21. A device for holding a patient's head in a prone or supine position according to claim 1 wherein said device further comprises a means for securely retaining the head in a fixed position.

22. A device for holding a patient's head in a prone or supine position according to claim 1 wherein said base comprises a means for holding the position of said device on a planar surface.

23. A device for holding a patient's head in a prone or supine position according to claim 21 where said retaining means comprises a web of material having a first and a second end, at least one end having a length of hook and loop fastener disposed thereon, and said device having at least one securing site comprising a corresponding length of hook and loop fastener disposed on said device such that said web circumscribes a portion of the patient's head and at least one end attaches to a securing site and said device to retain said head in a fixed position.

24. A device for holding a patient's head in a prone or supine position according to claim 22 wherein said holding means comprising one or more flanges attached to the base and extending downwardly therefrom.

25. A device for holding a patient's head in a prone or supine position according to claim 22 wherein said holding means comprises a plurality non-skid surfaces attached to the bottom surface of said device.

26. A device for holding a patient's head in a prone or supine position according to claim 1 wherein at least one said arcuate shaped plate further comprises a means for cushioning said head.

27. A device for holding a patient's head in a prone or supine position according to claim 14 wherein said dowel is a multi-sided polygon in transverse cross-section.

28. A device for holding a patient's head in a prone or supine position according to claim 6 wherein said dowels are capable of engaging said slots in said frame end positions in various positions so as to adjust the arcuate position of said support member.

* * * * *